(12) United States Patent
Aspuru-Guzik et al.

(10) Patent No.: US 9,972,795 B2
(45) Date of Patent: May 15, 2018

(54) ORGANIC LIGHT-EMITTING DIODE MATERIALS

(71) Applicants: President and Fellows of Harvard College, Cambridge, MA (US); Massachusetts Institute of Technology, Cambridge, MA (US)

(72) Inventors: Alan Aspuru-Guzik, Cambridge, MA (US); Rafael Gomez-Bombarelli, Cambridge, MA (US); Jorge Aguilera-Iparraguirre, Roslindale, MA (US); Marc Baldo, Lexington, MA (US); Troy Van Voorhis, Cambridge, MA (US); Timothy D. Hirzel, Quincy, MA (US); Matthias Bahlke, Somerville, MA (US); David McMahon, Cambridge, MA (US); Tony Chang-Chi Wu, Cambridge, MA (US)

(73) Assignees: Presidents and Fellows of Harvard College, Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days. days.

(21) Appl. No.: 15/310,241

(22) PCT Filed: May 13, 2015

(86) PCT No.: PCT/US2015/030600
§ 371 (c)(1),
(2) Date: Nov. 10, 2016

(87) PCT Pub. No.: WO2015/175680
PCT Pub. Date: Nov. 19, 2015

(65) Prior Publication Data
US 2017/0271601 A1   Sep. 21, 2017

Related U.S. Application Data

(60) Provisional application No. 61/996,836, filed on May 14, 2014.

(51) Int. Cl.
*H01L 51/00* (2006.01)
*C09K 11/06* (2006.01)
(Continued)

(52) U.S. Cl.
CPC ........ *H01L 51/0094* (2013.01); *C07D 209/86* (2013.01); *C07D 421/14* (2013.01);
(Continued)

(58) Field of Classification Search
CPC ............. H01L 51/0094; H01L 51/0069; H01L 51/007; H01L 51/0071; H01L 51/0072;
(Continued)

(56) References Cited

U.S. PATENT DOCUMENTS

2010/0184942 A1* 7/2010 Chen .................... C07D 209/82
528/423
2014/0124762 A1* 5/2014 Buchwald ........... H01L 51/0072
257/40
(Continued)

FOREIGN PATENT DOCUMENTS

CN    103694992 A    4/2014
DE    10 200602577 A1    12/2007
(Continued)

OTHER PUBLICATIONS

Blicke et al., "Diarsyls. II. Tetra-aryladiarsysls," This Journal Borgstrom and Dewar, 52: 780-786 (Feb. 1, 1930).
(Continued)

*Primary Examiner* — Nicholas Tobergte
(74) *Attorney, Agent, or Firm* — Alexander Akhiezer; Lucas Watkins; Foley Hoag LLP

(57) ABSTRACT

Described herein are molecules for use in organic light emitting diodes. Example molecules comprise at least one (Continued)

Scheme 3 moiety A and at least one moiety D. Values and preferred values of the moieties A and D are described herein. The molecules comprise at least one atom selected from Si, Se, Ge, Sn, P, or As.

25 Claims, 3 Drawing Sheets

(51) Int. Cl.
    *C07D 421/14*     (2006.01)
    *C07F 9/6571*     (2006.01)
    *C07F 9/6568*     (2006.01)
    *C07F 7/08*     (2006.01)
    *C07D 209/86*     (2006.01)
    *H01L 51/50*     (2006.01)

(52) U.S. Cl.
    CPC .......... *C07F 7/0814* (2013.01); *C07F 7/0816* (2013.01); *C07F 9/65683* (2013.01); *C07F 9/657163* (2013.01); *C09K 11/06* (2013.01); *H01L 51/007* (2013.01); *H01L 51/0069* (2013.01); *H01L 51/0071* (2013.01); *H01L 51/0072* (2013.01); *C09K 2211/1007* (2013.01); *C09K 2211/1014* (2013.01); *C09K 2211/1022* (2013.01); *C09K 2211/1044* (2013.01); *C09K 2211/1048* (2013.01); *C09K 2211/1055* (2013.01); *C09K 2211/1077* (2013.01); *C09K 2211/1081* (2013.01); *C09K 2211/1085* (2013.01); *H01L 51/5016* (2013.01); *H01L 2251/5376* (2013.01); *H01L 2251/552* (2013.01)

(58) Field of Classification Search
    CPC .... C07D 209/86; C07F 7/0814; C07F 7/0816; C07F 9/657163; C07F 9/65683; C09K 11/06
    See application file for complete search history.

(56) References Cited

U.S. PATENT DOCUMENTS

| | | | |
|---|---|---|---|
| 2015/0280147 A1* | 10/2015 | Wesemann | C09K 11/06 252/301.16 |
| 2017/0077420 A1* | 3/2017 | Li | C07F 9/5728 |
| 2017/0244049 A1* | 8/2017 | Aspuru-Guzik | H01L 51/0072 |

FOREIGN PATENT DOCUMENTS

| | | |
|---|---|---|
| EP | 2182038 A1 | 5/2010 |
| EP | 2709183 A1 | 3/2014 |
| WO | WO-2013/011955 A1 | 1/2013 |

OTHER PUBLICATIONS

Choi et al., "Synthesis and Characterization of Dibenzannulated Silole Dianions. The 1,1-dilithiosilafluorene and 1,1'-dilithiobis-(silafluorene) dianions1," Tetrahedron Lett, 41(35): 6685-6688 (Aug. 1, 2000).

Davis et al., "The Synthesis and Stereochemistry of 5,10-Disubstituted 5,10-Dihydrophosphanthrens and Their Derivatives," 3770-3785 (Jan. 1, 1964).

Mayr et al., "Efficiency Enhancement of Organic Light-Emitting Diodes Incorporating a Highly Oriented Thermally Activated Delayed Fluorescence Emitter," Adv Funct Mater, 24(33): 5232-5239 (Jun. 11, 2014).

Serevicius et al., "Enhanced Electroluminescence Based on Thermally Activated Delayed Fluorescence From a Carbazole-Triazine Derivative," Phys Chem Chem Phys, 15(38): 15850-15855 (Jan. 1, 2013).

* cited by examiner

ORGANIC LIGHT-EMITTING DIODE MATERIALS

RELATED APPLICATION

This application is the U.S. National Stage of International Application No. PCT/US2015/030600, filed May 13, 2015, which designates the U.S., published in English, and claims the benefit of U.S. Provisional Application No. 61/996,836, filed on May 14, 2014. The entire teachings of the above applications are incorporated herein by reference.

STATEMENT REGARDING FEDERALLY SPONSORED RESEARCH

This invention was made with Government support under Grant No. DE-FG02-07ER46474 awarded by the Department of Energy. The Government has certain rights in the invention.

BACKGROUND OF THE INVENTION

An organic light emitting diode (OLED) is a light-emitting diode (LED) in which a film of organic compounds is placed between two conductors and emits light in response to excitation, such as an electric current. OLEDs are useful in displays such as television screen, computer monitors, mobile phones, and tablets.

OLED materials rely on the radiative decay of molecular excited states (excitons) generated by recombination of electrons and holes in a host transport material. The nature of excitation results in interactions between electrons and holes that split the excited states into bright singlets (with a total spin of 0) and dark triplets (with a total spin of 1). Since the recombination of electrons and holes affords a statistical mixture of four spin states (one singlet and three triplet sublevels), conventional OLEDs have a maximum theoretical efficiency of 25%.

To date, OLED material design has focused on harvesting the remaining energy from the normally dark triplets into an emissive state. Recent work to create efficient phosphors, which emit light from the normally dark triplet state, have resulted in green and red OLEDs. Other colors such as blue, however, require higher energy excited states which enhance the degradation process of the OLED.

The fundamental limiting factor to the triplet-singlet transition rate is a value of the parameter $|H_{fi}/\Delta|^2$, where $H_{fi}$ is the coupling energy due to hyperfine or spin-orbit interactions, and $\Delta$ is the energetic splitting between singlet and triplet states. Traditional phosphorescent OLEDs rely on the mixing of singlet and triplet states due to spin-orbital (SO) interaction, increasing $H_{fi}$ and affording a lowest emissive state shared between a heavy metal atom and an organic ligand. This results in energy harvesting from all higher singlet and triplet states, followed by phosphorescence (relatively short-lived emission from the excited triplet). The shortened triplet lifetime reduces triplet exciton annihilation by charges and other excitons. Recent work by others suggests that the limit to the performance of phosphorescent materials has been reached.

SUMMARY OF THE INVENTION

Thus, a need exists for OLEDs which can reach higher excitation states without rapid degradation. It has now been discovered that thermally activated delayed fluorescence (TADF), which relies on minimization of $\Delta$ as opposed to maximization of $H_{fi}$, can transfer population between singlet levels and triplet sublevels in a relevant timescale, such as, for example, 110 μs. The compounds described herein are capable of fluorescing or phosphorescing at higher energy excitation states than compounds previously described.

Accordingly, in one embodiment, the present invention is a compound represented by any one of the following structural formulas:

(I)

(II)

(III)

(IV)

(V)

(VI)

(VII)

(VIII)

(IX)

(X)

In formulas (I) through (X), each D and each A, independently, are selected from the group consisting of:

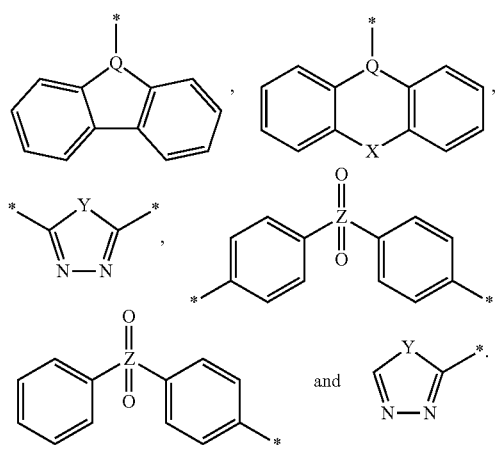

with the understanding that when more than one A or more than one D are present, all As and, independently, all Ds are the same. Further, in formulas (I) through (X), the (*) represents the point of attachment of the moieties A and D in the structural formulas (I) through (X), and the compound comprises at least one atom selected from Si, Se, Ge, Sn, P, or As.

In structural formulas (I)-(X) Q is N, P, or As; X is O, S, Se, $C(CH_3)_2$, or $Si(CH_3)_2$; Y is O, S, or Se; and Z is S or Se. Each structural formula (I)-(X) can be optionally substituted with with one or more substituents selected from $C_1$-$C_6$ alkyl, —$OCH_3$, —$SCH_3$, —$C(CH_3)_3$, —$Si(CH_3)_3$, —$Ge(CH_3)_3$, or —$Sn(CH_3)_3$.

In another embodiment, the present invention is an organic light-emitting device comprising a first electrode, a second electrode, and an organic layer between the first electrode and the second electrode. The organic layer comprises at least one light-emitting molecule represented by a structural formulas (I)-(X).

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
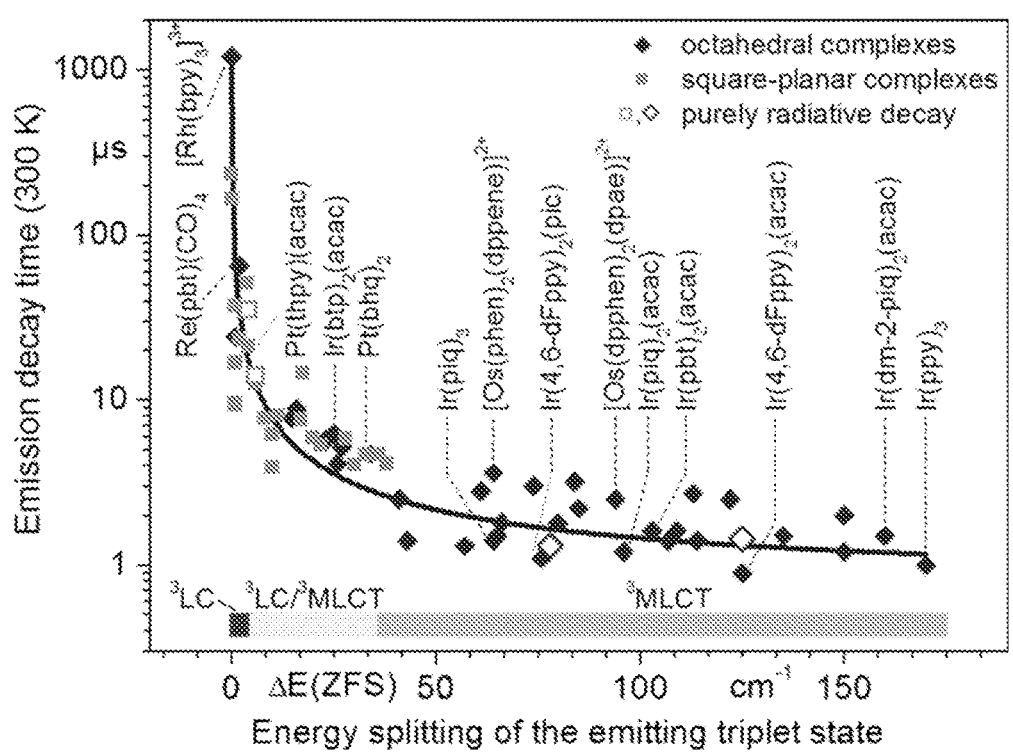
FIG. 1 is a scatter plot illustrating the relationship between the brightness of an OLED as compared to the time of decay after excitation. The plot illustrates that brightness of the OLED decreases as the time of decay increases.

A description of example embodiments of the invention follows.

Glossary

The term "alkyl," as used herein, refers to a saturated aliphatic branched or straight-chain monovalent hydrocarbon radical having the specified number of carbon atoms. Thus, "$C_1$-$C_6$ alkyl" means a radical having from 1-6 carbon atoms in a linear or branched arrangement. Examples of "$C_1$-$C_6$ alkyl" include , n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl. Alkyl can be optionally substituted with halogen, —OH, $C_1$-$C_6$ alkyl, $C_1$-$C_6$ alkoxy, —$NO_2$, —CN, and —$N(R^1)(R^2)$ wherein $R^1$ and $R^2$ are each independently selected from —H and $C_1$-$C_3$ alkyl.

The term "alkoxy", as used herein, refers to an "alkyl-O-" group, wherein alkyl is defined above. Examples of alkoxy group include methoxy or ethoxy groups. The "alkyl" portion of alkoxy can be optionally substituted as described above with respect to alkyl.

The terms "halogen," as used herein, refer to fluorine, chlorine, bromine, or iodine.

The term "symmetrical molecule," as used herein, refers to molecules that are group symmetric or synthetic symmetric. The tettn "group symmetric," as used herein, refers to molecules that have symmetry according to the group theory of molecular symmetry. The term "synthetic symmetric," as used herein, refers to molecules that are selected such that no regioselective synthetic strategy is required.

The term "donor," as used herein, refers to a molecular fragment that can be used in organic light emitting diodes and is likely to donate electrons from its highest occupied molecular orbital to an acceptor upon excitation. In an example embodiment, donors have an ionization potential greater than or equal to −6.5 eV.

The term "acceptor," as used herein, refers to a molecular fragment that can be used in organic light emitting diodes and is likely to accept electrons into its lowest unoccupied molecular orbital from a donor that has been subject to excitation. In an example embodiment, acceptors have an electron affinity less than or equal to −0.5 eV.

The term "bridge," as used herein, refers to a π-conjugated molecular fragment that can be included in a molecule which is covalently linked between acceptor and donor moieties. The bridge can, for example, be further conjugated to the acceptor moiety, the donor moiety, or both. Without being bound to any particular theory, it is believed that the bridge moiety can sterically restrict the acceptor and donor moieties into a specific configuration, thereby preventing the overlap between the conjugated π system of donor and acceptor moieties. Examples of suitable bridge moieties include phenyl.

Principles of OLED

OLEDs are typically composed of a layer of organic materials or compounds between two electrodes, an anode and a cathode. The organic molecules are electrically conductive as a result of delocalization of π electronics caused by conjugation over part or all of the molecule. When voltage is applied, electrons from the highest occupied molecular orbital (HOMO) present at the anode flow into the lowest unoccupied molecular orbital (LUMO) of the organic molecules present at the cathode. Removal of electrons from the HOMO is also referred to as inserting electron holes into the HOMO. Electrostatic forces bring the electrons and the holes towards each other until they recombine and form an exciton (which is the bound state of the electron and the hole). As the excited state decays and the energy levels of the electrons relax, radiation is emitted in the form of light with a frequency in the visible spectrum. The frequency of this radiation depends on the band gap of the material, which is the difference in energy between the HOMO and the LUMO.

As electrons and holes are fermions with half integer spin, an exciton may either be in a singlet state or a triplet state depending on how the spins of the electron and hole have been combined. Statistically, three triplet excitons will be formed for each singlet exciton. Decay from triplet states is spin forbidden, which results in increases in the timescale of the transition and limits the internal efficiency of fluorescent devices. Phosphorescent organic light-emitting diodes make use of spin-orbit interactions to facilitate intersystem crossing between singlet and triplet states, thus obtaining emission from both singlet and triplet states and improving the internal efficiency.

The prototypical phosphorescent material is iridium tris (2-phenylpyridine) (Ir(ppy)$_3$) in which the excited state is a charge transfer from the Ir atom to the organic ligand. Such approaches have reduced the triplet lifetime to about 1 µs, several orders of magnitude slower than the radiative lifetimes of fully-allowed transitions such as fluorescence. Ir-based phosphors have proven to be acceptable for many display applications, but losses due to large triplet densities still prevent the application of OLEDs to solid-state lighting at higher brightness.

Further, recent research suggests that traditional Iridium based OLEDs may have reached a physical performance limit. As illustrated in FIG. 1, the brightness of an OLED will decrease as the time of decay increases. Since the highest energy triplet state is the origin of the luminescent transition in the Ir-based materials of FIG. 1, increasing the zero-field splitting through additional spin-orbit coupling will eventually lengthen the effective lifetime of the other two triplets. It is believed that this effect is responsible for the asymptote empirically observed at about 1 µs.

The recently developed thermally activated delayed fluorescence (TADF) seeks to minimize energetic splitting between singlet and triplet states (Δ). The reduction in exchange splitting from typical values of 0.4-0.7 eV to a gap of the order of the thermal energy (proportional to $k_B T$, where $k_B$ represents the Boltzmann constant, and T represents temperature) means that thermal agitation can transfer population between singlet levels and triplet sublevels in a relevant timescale even if the coupling between states is small.

Example TADF molecules consist of donor and acceptor moieties connected directly by a covalent bond or via a conjugated linker (or "bridge"), such as a phenyl ring. A "donor" moiety is likely to transfer electrons from its HOMO upon excitation to the "acceptor" moiety. An "acceptor" moiety is likely to accept the electrons from the "donor" moiety into its LUMO. The donor-acceptor nature of TADF molecules results in low-lying excited states with charge-transfer character that exhibit very low Δ. Since thermal molecular motions can randomly vary the optical properties of donor-acceptor systems, a rigid three-dimensional arrangement of donor and acceptor moieties can be used to limit the non-radiative decay of the charge-transfer state by internal conversion during the lifetime of the excitation.

It is desirable, therefore, to increase spin-orbital coupling by creating a system with a low singlet-triplet gap which increases reversed intersystem crossing (RISC) while decreasing phosphorescence emissions lifetimes. While traditional OLED systems rely on heavy metals, such as Ir, the instability of the metal organic complex and high cost of raw materials leaves room for improvement. Accordingly, without being bound to any particular theory, it is believed that use of non-metal, semimetal, and non-transition metal atoms from the second, third, fourth, and fifth row of the periodic table (e.g., N, O, S, Si, Ge, Sn, P, Se, or As), can be used to increase the spin orbit-coupling. Relying on these atoms instead of heavy metal atoms will avoid the problems recited above.

Compounds of the Invention

The molecules of the present invention, when excited via theinial or electronic means, can produce light in the visible region of the spectrum such as blue or green. The desired spin-orbit/thermally activated delayed fluorescence (SO/TADF) materials proposed herein can be achieved by incorporating or otherwise introducing functionalization of donor and acceptor moieties with non-metal, semimetal, and non-transition metal atoms from the second, third, fourth, and fifth row of the periodic table. It has been discovered that use of these atoms, such as Si, Se, Ge, Sn, P, or As, achieve improved spin-orbit/thermally activated delayed fluorescence over second and third row non-metals such as N, O, or S.

Table 1 illustrates example moieties suitable to function as either acceptor or donor moieties in SO/TADF OLED materials, predicted HOMO and LUMO orbital energies, and predicted zero-field splitting (ZFS, D) for a localized triplet state. The properties for a moiety with only a second or third row non-metal, such as N, O, or S were calculated first. Substitution of the second row or third row atoms with non-metals, metalloids, and non-transition metals from the third, fourth, or fifth row showed a desirable shift in the HOMO and LUMO values, as well as the ZFS.

TABLE 1

| | HOMO (eV) | LUMO (eV) | D (cm$^{-1}$) |
|---|---|---|---|
| 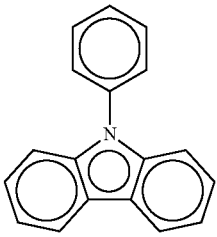 | -5.00 | -1.70 | 0.03 |
| 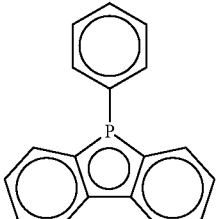 | -5.11 | -2.29 | 0.04 |
| 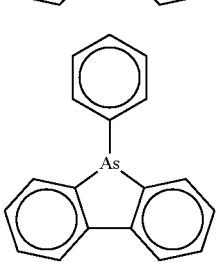 | -5.11 | -2.31 | -0.73 |

TABLE 1-continued
| | HOMO (eV) | LUMO (eV) | D (cm⁻¹) |
|---|---|---|---|
| 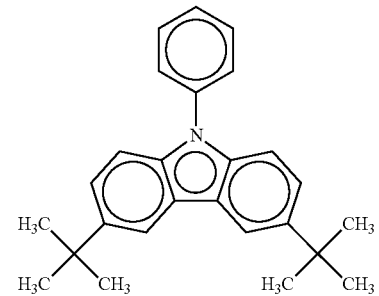 | -4.82 | -1.74 | 0.02 |
| 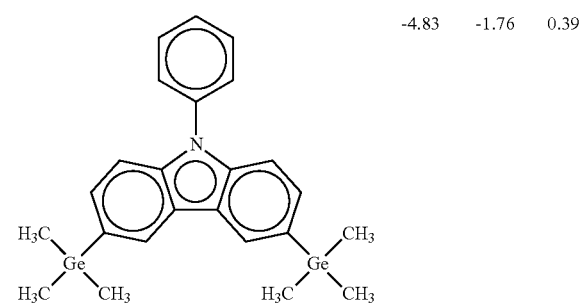 | -4.82 | -1.75 | -0.04 |
| | -4.83 | -1.76 | 0.39 |
| | -4.82 | -1.77 | 5.08 |
| 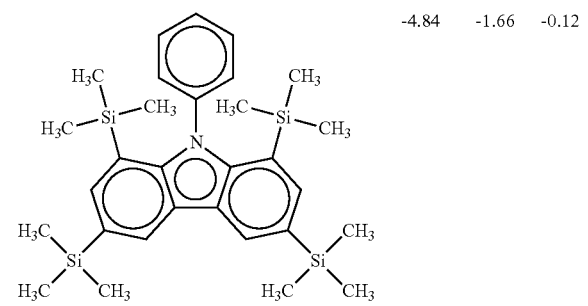 | -4.84 | -1.66 | -0.12 |
TABLE 1-continued
| | HOMO (eV) | LUMO (eV) | D (cm⁻¹) |
|---|---|---|---|
| 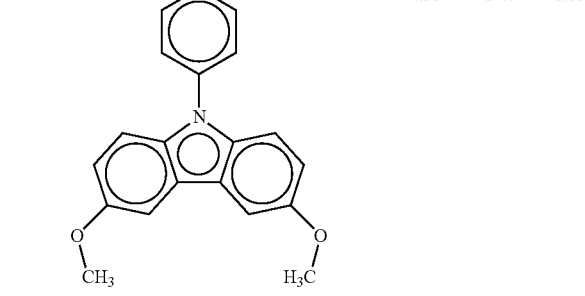 | -4.35 | -1.47 | 0.03 |
| | -4.25 | -1.54 | -0.73 |
| 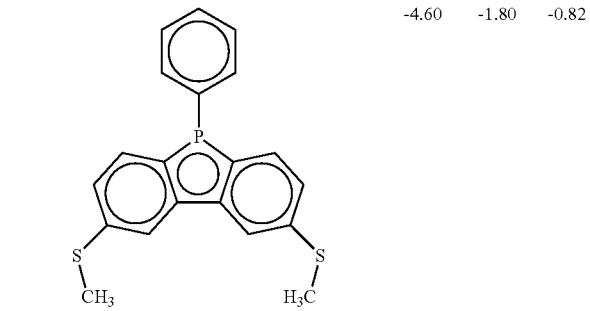 | -4.60 | -1.80 | -0.82 |
| | -4.85 | -2.10 | -0.85 |
| 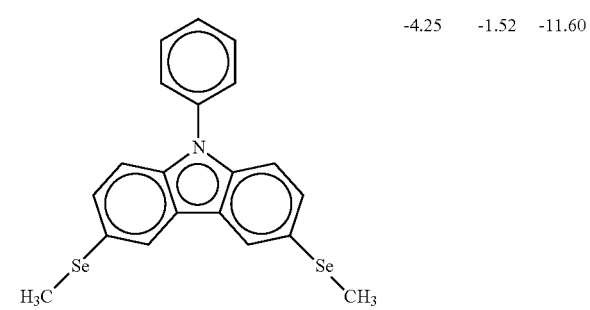 | -4.25 | -1.52 | -11.60 |

TABLE 1-continued
| | HOMO (eV) | LUMO (eV) | D (cm⁻¹) |
|---|---|---|---|
| 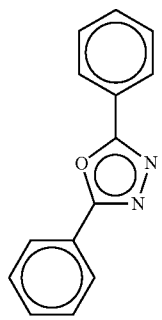 | -5.25 | -2.85 | 0.02 |
| 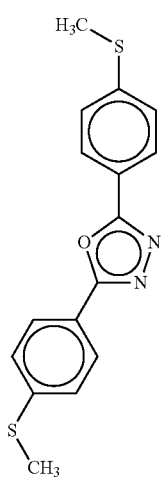 | -4.60 | -2.43 | -0.76 |
| 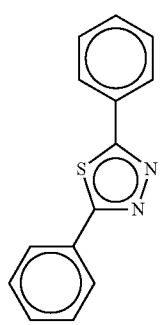 | -5.20 | -3.01 | -0.40 |
| 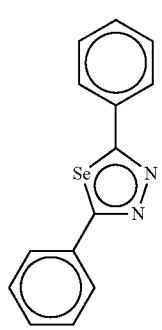 | -5.18 | -3.06 | -6.16 |
TABLE 1-continued
| | HOMO (eV) | LUMO (eV) | D (cm⁻¹) |
|---|---|---|---|
| 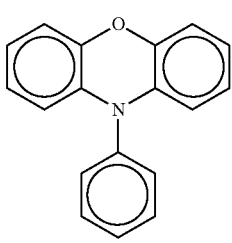 | -5.06 | -2.35 | -0.02 |
| 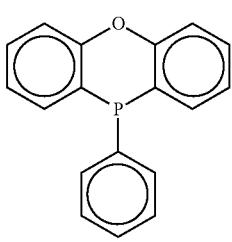 | -3.95 | -2.84 | -1.23 |
| 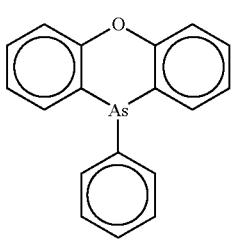 | -4.89 | -1.84 | -3.07 |
| 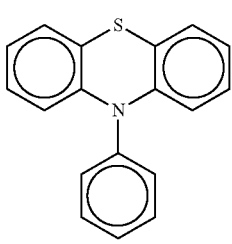 | -4.10 | -1.70 | -0.56 |
| 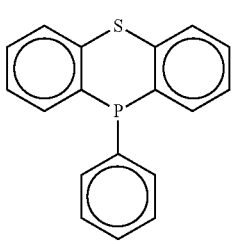 | -4.49 | -1.95 | -0.74 |
| 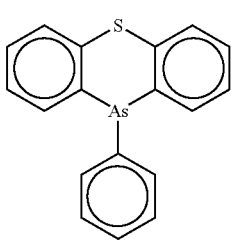 | -4.75 | -1.94 | -2.10 |

TABLE 1-continued

| | HOMO (eV) | LUMO (eV) | D (cm$^{-1}$) |
|---|---|---|---|
| 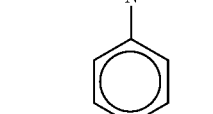 | -4.17 | -1.73 | -9.89 |
| 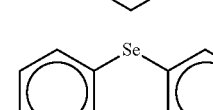 | -4.49 | -1.95 | -9.44 |
| 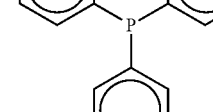 | -4.76 | -1.96 | -14.49 |
| 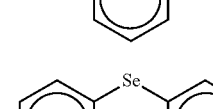 | -5.81 | -3.26 | -0.27 |
| 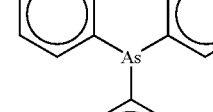 | -5.82 | -4.62 | -7.29 |
| 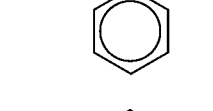 | -6.59 | -1.32 | -0.09 |

TABLE 1-continued

| | HOMO (eV) | LUMO (eV) | D (cm$^{-1}$) |
|---|---|---|---|
| | -4.68 | -1.45 | -0.02 |
| | -4.65 | -1.46 | -0.49 |
| | -4.07 | -2.77 | 0.72 |
| | -3.99 | -3.30 | 54.37 |

Given the calculated values for the example moieties identified in Table 1, it is believed that construction of a molecule comprising at least two moieties in Table 1 covalently bound, either directly or via a conjugated linker (or "bridge"), will result in OLEDs that demonstrate that desired properties described above.

Accordingly, in one embodiment, the present invention is a compound represented by any one of the following structural formulas:

$$A-D \quad (I)$$

$$A-A \quad (II)$$

$$\underset{A}{\overset{D-A}{|}} \quad (III)$$

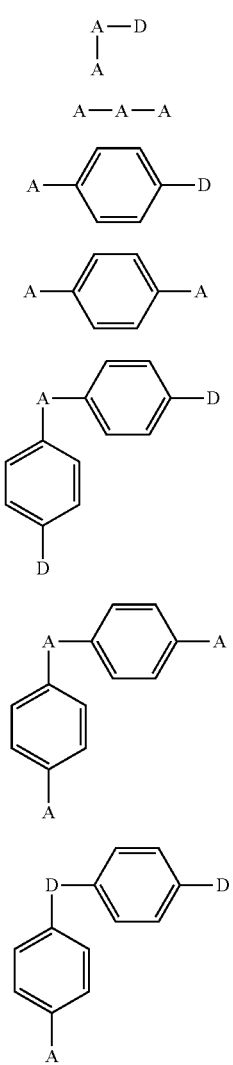

In formulas (I) through (X), each D and each A, independently, are selected from the group consisting of:

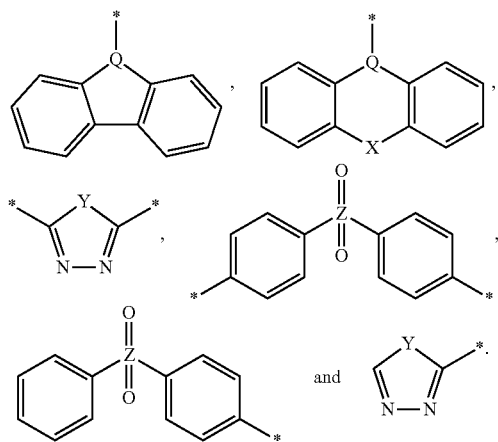

with the understanding that when more than one A or more than one D are present, all As and, independently, all Ds are the same. Further, in formulas (I) through (X), the (*) represents the point of attachment of the moieties A and D in the structural formulas (I) through (X), and the compound comprises at least one atom selected from Si, Se, Ge, Sn, P, or As. For example, the compound comprises at least one atom selected from Si, Se, or P. In an example embodiment, the compound comprises at least one atom selected from. Si or Se. In another example embodiment, the compound comprises Si.

The moiety A and the moiety D, for each occurrence independently, are optionally substituted with one or more substituents selected from $C_1$-$C_6$ alkyl, —$OCH_3$, —$SCH_3$, —$C(CH_3)_3$, —$Si(CH_3)_3$, —$Ge(CH_3)_3$, or —$Sn(CH_3)_3$. For example, the moiety A and the moiety D, for each occurrence independently, are optionally substituted with one or more substituents selected from $C_1$-$C_6$ alkyl, —$OCH_3$, —$C(CH_3)_3$, or —$Si(CH_3)_3$. In an example embodiment, the moiety A and the moiety D for each occurrence independently, are optionally substituted with one or more substituents selected from $C_1$-$C_6$ alkyl or —$Si(CH_3)_3$ In another example embodiment, the moiety A and the moiety D for each occurrence independently, are optionally substituted with —$Si(CH_3)_3$.

In structural formulas (I)-(X) of the present invention:

Q is N, P, or As. For example Q is N or P. In an example embodiment, Q is N.

X is O, S, Se, $C(CH_3)_2$, or $Si(CH_3)_2$. For example, X is O, $C(CH_3)_2$, or $Si(CH_3)_2$. In an example embodiment, X is O or $C(CH_3)_2$. In another example embodiment, X is O.

Y is O, S, or Se. For example, Y is O or Se. In an example embodiment, Y is Se.

Z is S or Se. For example, Z is Se.

In another example embodiment, the compound is represented by any one of the following structural formulas:

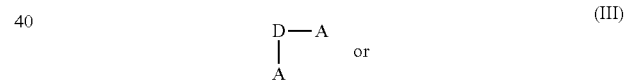

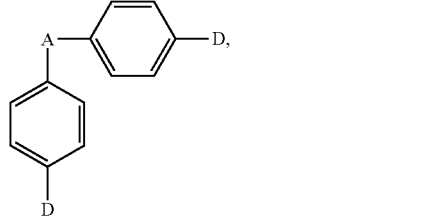

wherein the values and examples values of the remaining variables are defined above with respect to formulas (I)-(X).

In another example embodiment, each moiety D and each moiety A, independently, are selected from the group consisting of:

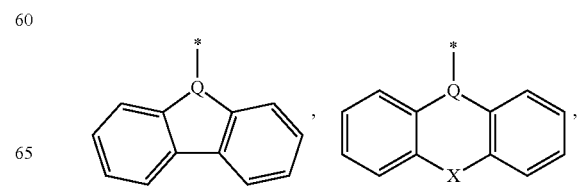

-continued

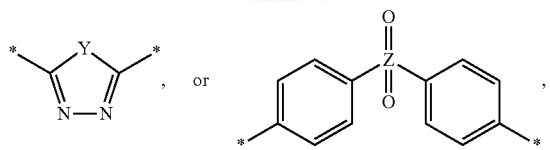

optionally substituted with one or more substituents selected from C$_1$-C$_6$ alkyl, —OCH$_3$, —CH$_3$, —C(CH$_3$)$_3$, —Si(CH$_3$)$_3$, —Ge(CH$_3$)$_3$, or —Sn(CH$_3$)$_3$, and wherein the values and example values of the remaining variables are defined above with respect to structural founulas (I)-(X).

In another example embodiment, at least one of the moieties A or D is

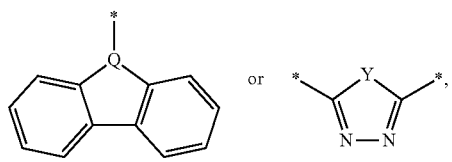

optionally substituted with one or more substituents selected from C$_1$-C$_6$ alkyl, —OCH$_3$, —CH$_3$, —C(CH$_3$)$_3$, —Si(CH$_3$)$_3$, —Ge(CH$_3$)$_3$, or —Sn(CH$_3$)$_3$, and wherein the values and example values of the remaining variables are the defined above with respect to structural formulas (I)-(X).

In another example embodiment, at least one of the moieties A or D is

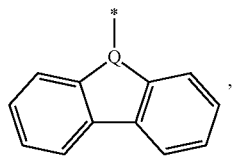

optionally substituted with one or more substituents selected from C$_1$-C$_6$ alkyl, —OCH$_3$, —CH$_3$, —C(CH$_3$)$_3$, —Si(CH$_3$)$_3$, —Ge(CH$_3$)$_3$, or —Sn(CH$_3$)$_3$, and wherein the values and example values of the remaining variables are the same as those defined above with respect to structural formulas (I)-(X).

In another example embodiment, at least one of the moieties A or D is

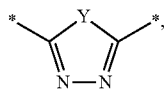

optionally substituted with one or more substituents selected from C$_1$-C$_6$ alkyl, —OCH$_3$, —CH$_3$, —C(CH$_3$)$_3$, —Si(CH$_3$)$_3$, —Ge(CH$_3$)$_3$, or —Sn(CH$_3$)$_3$, and wherein the values and example values of the remaining variables are the same as those defined above with respect to structural formulas (I)-(X).

In another example embodiment, at least one of the moieties A or D is

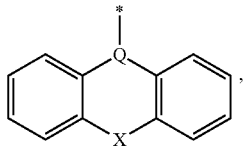

optionally substituted with one or more substituents selected from C$_1$-C$_6$ alkyl, —OCH$_3$, —CH$_3$, —C(CH$_3$)$_3$, —Si(CH$_3$)$_3$, —Ge(CH$_3$)$_3$, or —Sn(CH$_3$)$_3$, and wherein the values and example values of the remaining variables are the same as those defined above with respect to structural formulas (I)-(X).

In another example embodiment, at least one of the moieties A or D is

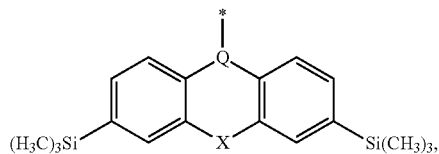

wherein the values and example values of the remaining variables are the same as those defined above with respect to structural formulas (I)-(X).

In another example embodiment, at least one of the moieties A or D is

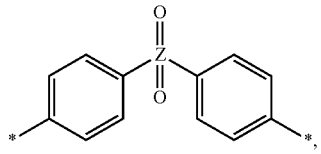

optionally substituted with one or more substituents selected from C$_1$-C$_6$ alkyl, —OCH$_3$, —CH$_3$, —C(CH$_3$)$_3$, —Si(CH$_3$)$_3$, —Ge(CH$_3$)$_3$, or —Sn(CH$_3$)$_3$, and wherein the values and example values of the remaining variables are the same as those defined above with respect to structural formulas (I)-(X).

In another example embodiment of the present invention, Z is Se, and the values and example values of the remaining variables are the same as those defined above with respect to structural formulas (I)-(X).

In another example embodiment of the present invention, Q is N or P, and the values and example values of the remaining variables are the same as those defined above with respect to structural formulas (I)-(X).

In another example embodiment of the present invention, Q is N, and the values and example values of the remaining variables are the same as those defined above with respect to structural formulas (I)-(X).

In another example embodiment of the present invention, X is O, C(CH$_3$)$_2$, or Si(CH$_3$)$_2$, and the values and example values of the remaining variables are the same as those defined above with respect to structural formulas (I)-(X).

In another example embodiment of the present invention, X is O or C(CH$_3$)$_2$, and the values and example values of the remaining variables are the same as those defined above with respect to structural formulas (I)-(X).

In another example embodiment of the present invention, X is O, and the values and example values of the remaining variables are the same as those defined above with respect to structural formulas (I)-(X).

In another example embodiment of the present invention, Y is O or Se, and the values and example values of the remaining variables are the same as those defined above with respect to structural formulas (I)-(X).

In another example embodiment of the present invention, Y is Se, and the values and example values of the remaining variables are the same as those defined above with respect to structural formulas (I)-(X).

In another example embodiment of the present invention, the compound of structural formulas (I)-(X) comprises at least one atom selected from Si, Se, or P, and wherein the values and example values of the remaining variables are defined above with respect to structural formulas (I)-(X).

In another example embodiment of the present invention, the compound of structural formulas (I)-(X) comprises at least one atom selected from Si or Se, and wherein the values and example values of the remaining variables are defined above with respect to structural formulas (I)-(X).

In another example embodiment of the present invention, the compound of structural formulas (I)-(X) comprises Si, and wherein the values and example values of the remaining variables are defined above with respect to structural formulas (I)-(X).

In another example embodiment of the present invention, the moiety A and the moiety D, for each occurrence independently, are substituted with $C_1$-$C_6$ alkyl, —$OCH_3$, —$C(CH_3)_3$, or —$Si(CH_3)_3$, and wherein the values and example values of the remaining variables are the same as those defined above with respect to structural formulas (I)-(X).

In another example embodiment of the present invention, the moiety A and the moiety D, for each occurrence independently, are substituted with $C_1$-$C_6$ alkyl or —$Si(CH_3)_3$, and wherein the values and example values of the remaining variables are the same as those defined above with respect to structural formulas (I)-(X).

In another example embodiment of the present invention, the moiety A and the moiety D, for each occurrence independently, are optionally substituted with —$Si(CH_3)_3$, and wherein the values and example values of the remaining variables are the same as those defined above with respect to structural formulas (I)-(X).

In another example embodiment of the present invention, the compound is represented by a structural formula selected from Compounds 1-20 as represented in Table 2.

TABLE 2

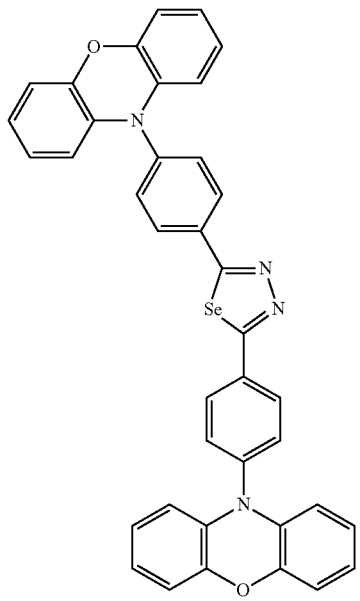 [SMILES: c1ccc2c(c1)Oc1ccccc1N2c1ccc(-c2nnc(-c3ccc(N4c5ccccc5Oc5ccccc54)cc3)[se]2)cc1]

Compound No. 1

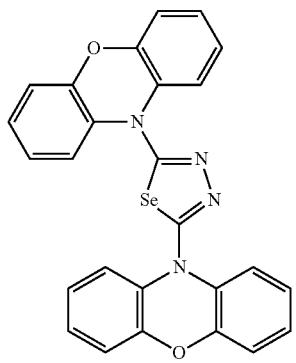 [SMILES: c1ccc2c(c1)Oc1ccccc1N2c1nnc(N2c3ccccc3Oc3ccccc32)[se]1]

Compound No. 2

TABLE 2-continued
Compound No. 3
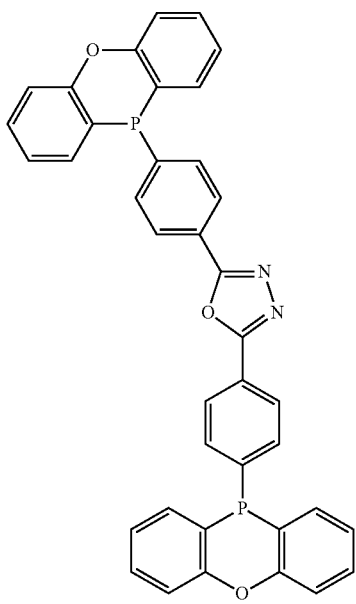 [SMILES: c1ccc2c(c1)Oc1ccccc1P2c1ccc(-c2nnc(-c3ccc(P4c5ccccc5Oc5ccccc54)cc3)o2)cc1]
Compound No. 4
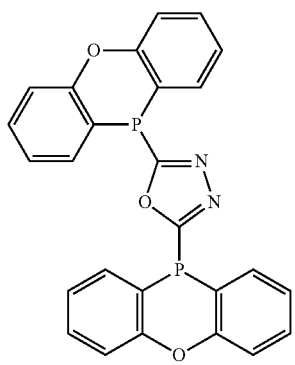 [SMILES: c1ccc2c(c1)Oc1ccccc1P2c1nnc(P2c3ccccc3Oc3ccccc32)o1]
Compound No. 5
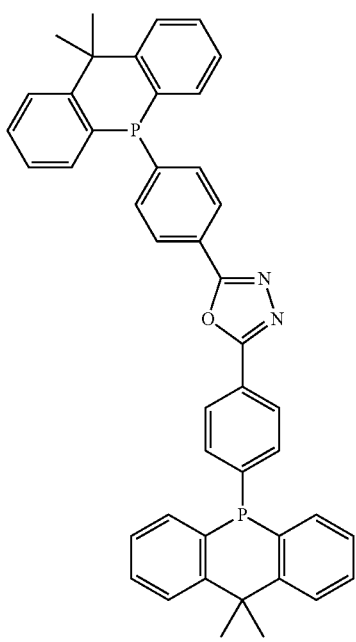 [SMILES: CC1(C)c2ccccc2P(c2ccc(-c3nnc(-c4ccc(P5c6ccccc6C(C)(C)c6ccccc65)cc4)o3)cc2)c2ccccc21]

TABLE 2-continued
Compound No. 6
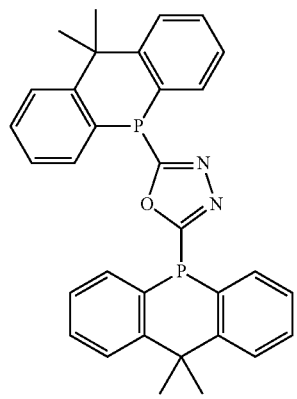 [SMILES: CC1(C)c2ccccc2P(c2nnc(P3c4ccccc4C(C)(C)c4ccccc43)o2)c2ccccc21]
Compound No. 7
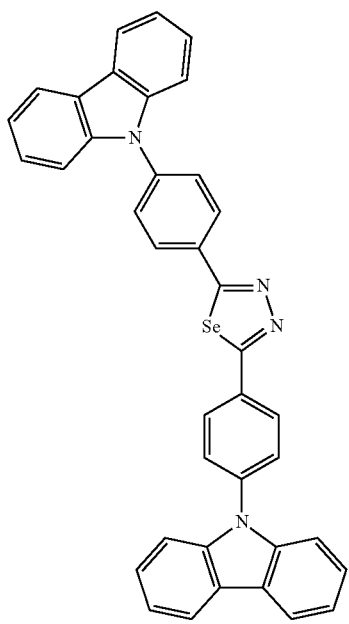 [SMILES: c1ccc2c(c1)c1ccccc1n2-c1ccc(-c2nnc(-c3ccc(-n4c5ccccc5c5ccccc54)cc3)[se]2)cc1]
Compound No. 8
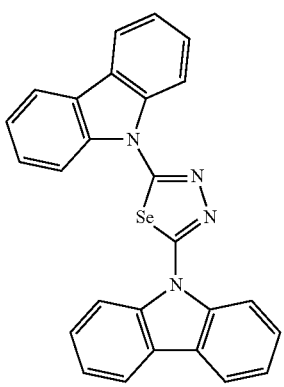 [SMILES: c1ccc2c(c1)c1ccccc1n2-c1nnc(-n2c3ccccc3c3ccccc32)[se]1]

TABLE 2-continued
Compound No. 9
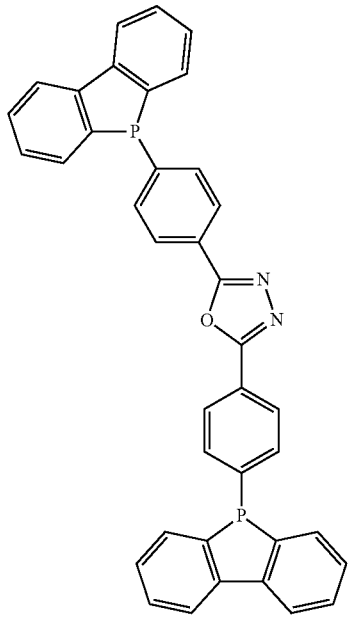 [SMILES: c1ccc2c(c1)c1ccccc1p2-c1ccc(-c2nnc(-c3ccc(-p4c5ccccc5c5ccccc54)cc3)o2)cc1]
Compound No. 10
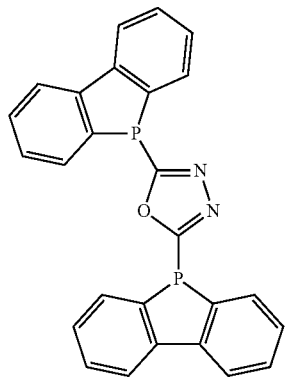 [SMILES: c1ccc2c(c1)c1ccccc1p2-c1nnc(-p2c3ccccc3c3ccccc32)o1]
Compound No. 11
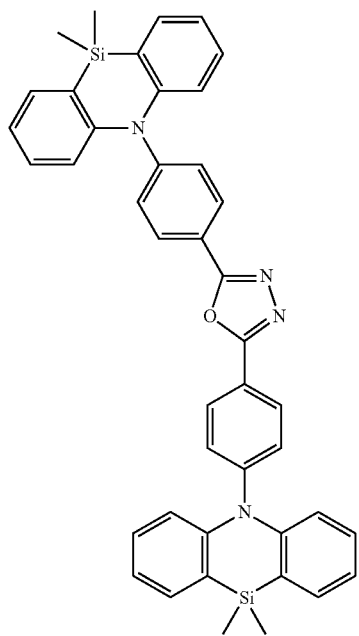 [SMILES: C[Si]1(C)c2ccccc2N(c2ccc(-c3nnc(-c4ccc(N5c6ccccc6[Si](C)(C)c6ccccc65)cc4)o3)cc2)c2ccccc21]

TABLE 2-continued
Compound No. 12
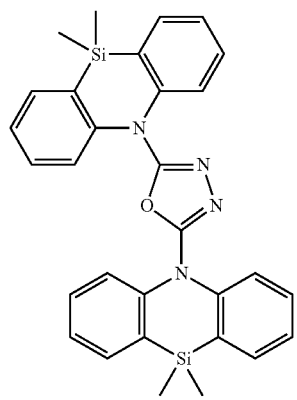 [SMILES: C[Si]1(C)c2ccccc2N(c2nnc(N3c4ccccc4[Si](C)(C)c4ccccc43)o2)c2ccccc21]
Compound No. 13
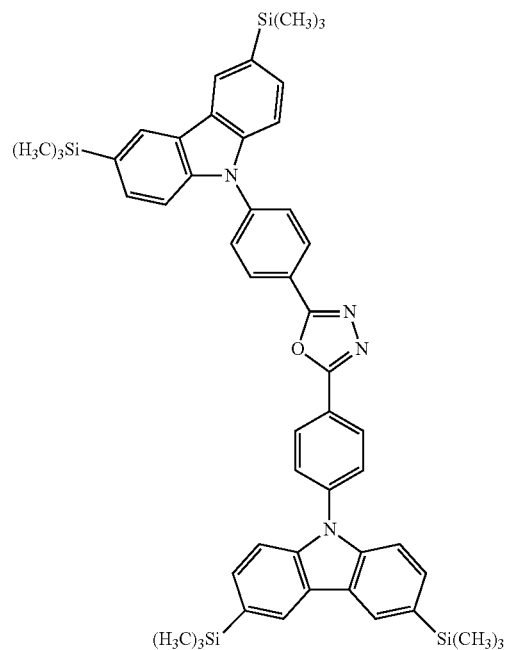
Compound No. 14
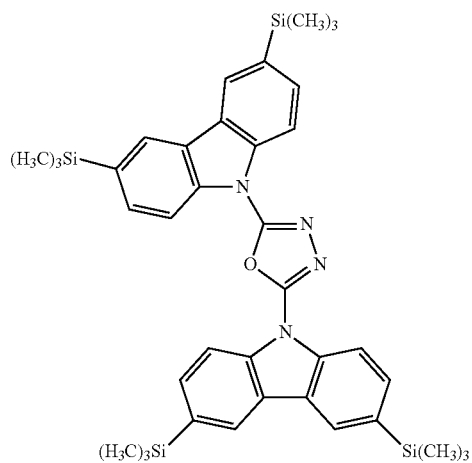

TABLE 2-continued
Compound No. 15
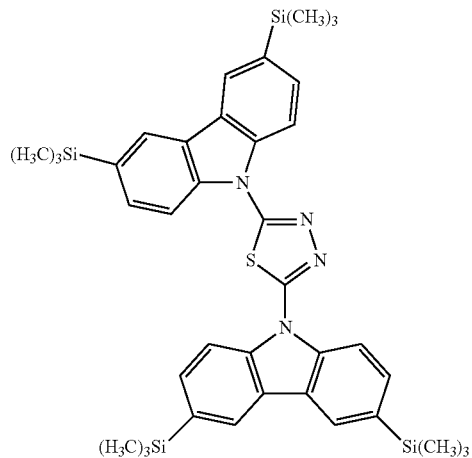
Compound No. 16
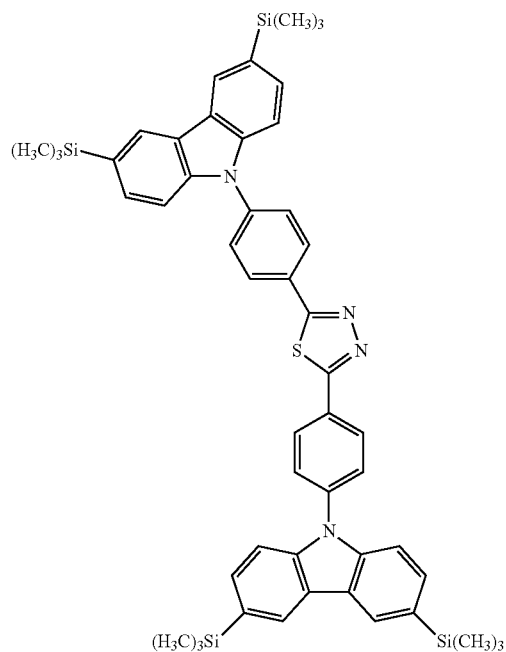

Compound No. 17
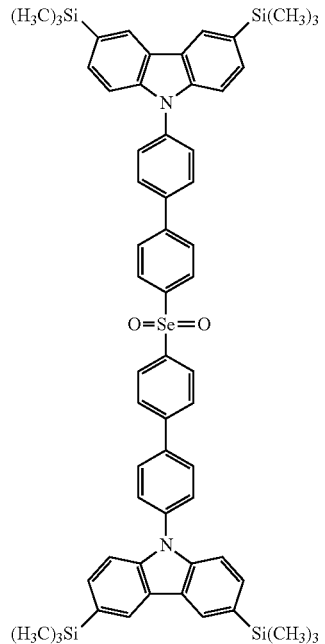
Compound No. 18
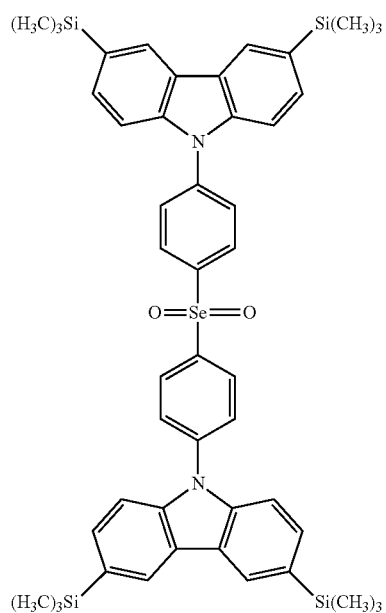

TABLE 2-continued

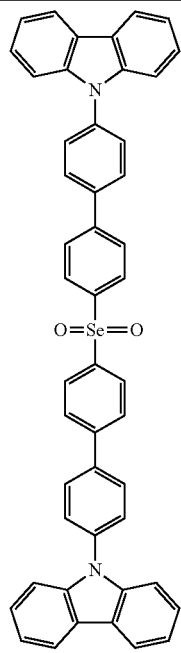

Compound No. 19

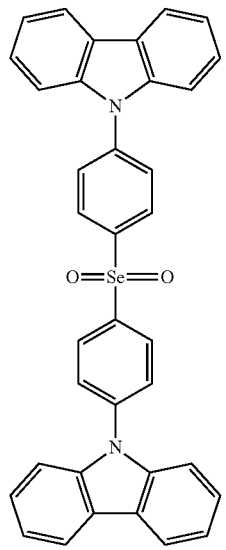 [SMILES: O=[Se](=O)(c1ccc(-n2c3ccccc3c3ccccc32)cc1)c1ccc(-n2c3ccccc3c3ccccc32)cc1]

Compound No. 20

In another embodiment, the present invention is an organic light-emitting device comprising a first electrode, a second electrode, and an organic layer between the first electrode and the second electrode. The organic layer comprises at least one light-emitting molecule represented by structural formulas (I)-(X).

Combinatorial Assembly and Screening

Example molecules of the present invention having desirable properties, such as color of visible emission, can be constructed from the moieties described above using a combinatorial process described below. While only two compounds are illustrated below, it is understood that different combinations of different moieties can be used to create a combinatorial library of compounds. The example moieties below are intended only to illustrate the concepts described herein, and are not intended to be limiting.

In the first step, a library of chemical moieties are screened for their abilities to function as an acceptor or donor moiety. Example properties examined include desirable quantum mechanical computations such as the ionization potential of the highest occupied molecular orbital (i.e., a "donor" moiety) and the electron affinity of the lowest unoccupied molecular orbital (i.e., an "acceptor" moiety). An example donor moiety selected after screening could be:

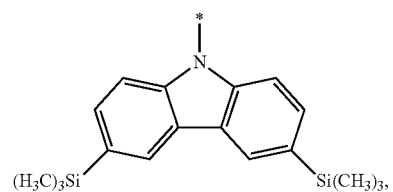

and an example acceptor moiety selected after screening could be:

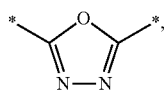

wherein (*) represents a point of attachment for the donor and acceptor moieties to each other or to an optional bridge moiety. The example acceptor moiety has two points of attachment in the present example. The same moieties will be attached at each point of attachment on the acceptor moiety, so that the resulting compound will be group symmetric.

In a second, optional, step the donor moiety is combined with a "bridge" moiety and an acceptor moiety is combined with a bridge moiety. The bridge moiety has two points of attachment, as illustrated below:

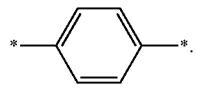

While the bridge moiety has two points of attachment, it only attaches to either a donor moiety or an acceptor moiety at one point of attachment during this step. The resulting combination of the example moieties would be:

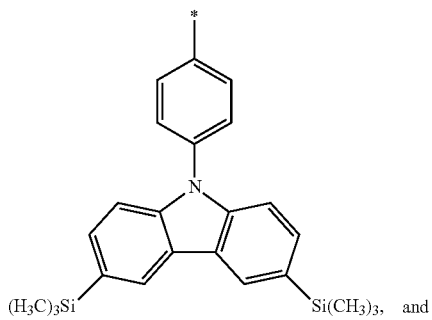

and

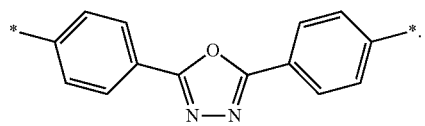

In a third step, the unattached point on the bridge moieties combine only with either a donor moiety or an acceptor moiety that does not have a bridge moiety currently attached. Donor moieties with a bridge moiety, therefore, will only attach to acceptor moieties. Acceptor moieties with a bridge moiety, therefore, will only attach to donor moieties. Using the examples above, the donor moiety with a bridge attached is represented by:

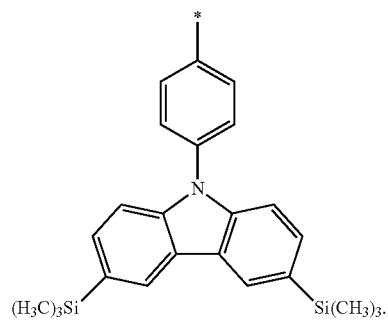

The acceptor without a bridge is represented by:

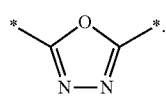

Combination of these moieties will result in the following complete molecule:

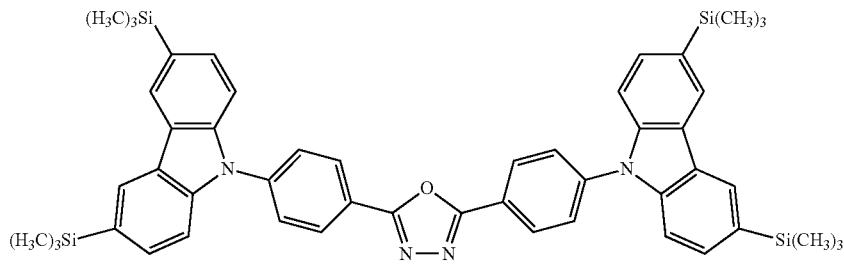

In a fourth step, the donor moiety without a bridge and an acceptor moiety without a bridge are combined. Using the example donor moiety and the example acceptor moiety identified above, combining the two moieties at their respective points of attachment would result in the following complete molecule:

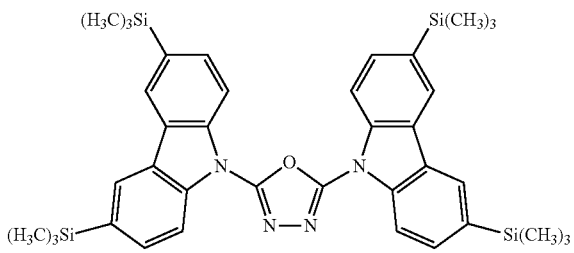

In the fifth step, the combined potential donors, acceptors, and bridges are screened based on quantum mechanical computations such as desired HOMO and LUMO values, as well as ZFS, vertical absorption (the energy required to excite the molecule from the ground state to the excited state), rate of decay (S1 to S0 oscillator strength, e.g., how fast and/or how bright the molecule's emission after excitation), estimated color of visible light emission in nanometers, and the singlet-triplet gap (the energy difference between the lowest singlet excited state, S1, the lowest triplet excited state, T1). Examples of these calculations for molecules embodied in the present invention are provided in Table 3.

TABLE 3

| Compound No. | HOMO (eV) | LUMO (eV) | Vertical Absorption (eV) | Emission (nm) | S1-T1 gap (eV) | S1-S0 oscillator strength |
|---|---|---|---|---|---|---|
| 3 | −5.84 | −1.86 | 3.49 | 406 | 0.732 | 0.002 |
| 4 | −5.99 | −1.23 | 4.06 | 365 | 0.584 | 0.002 |
| 5 | −5.8 | −1.79 | 3.48 | 407 | 0.729 | 0.117 |
| 6 | −6.09 | −0.94 | 4.38 | 345 | 0.798 | 0.001 |
| 9 | −6 | −1.91 | 3.67 | 392 | 0.914 | 0.504 |
| 10 | −6.17 | −1.28 | 4.34 | 348 | 1.315 | 0.006 |
| 11 | −5.19 | −1.98 | 2.7 | 480 | 0.008 | 0.001 |
| 12 | −5.52 | −0.6 | 4.28 | 352 | 0.784 | 0.196 |
| 13 | −5.44 | −1.9 | 3.08 | 441 | 0.5 | 0.865 |
| 14 | −5.53 | −1.02 | 3.93 | 374 | 0.779 | 0.492 |
| 16 | −5.41 | −2.17 | 2.82 | 468 | 0.485 | 0.901 |

Exemplification

Synthesis of Compound No. 13

Figure 2:
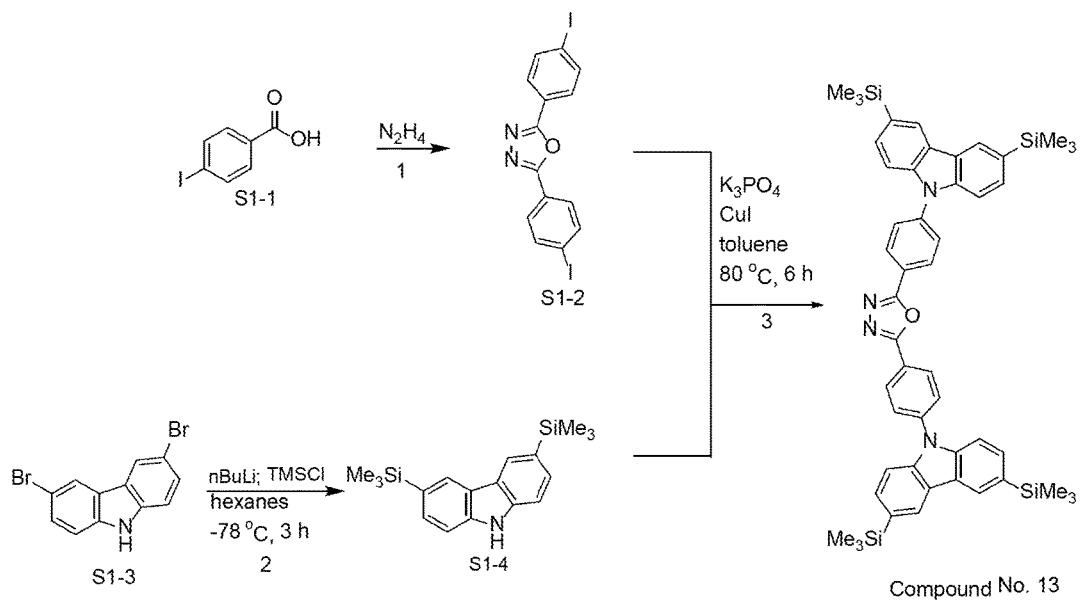
FIG. 2 is a synthetic scheme (Scheme 1) illustrating synthesis of an example embodiment of the present invention.

Compound No. 13 can be synthesized by a person of ordinary skill following Scheme 1 illustrated in FIG. 2. The starting materials S1-1 and S1-3 are available for purchase from Acros Organics (S1-1: CAS No. 619-58-9; S1-3: CAS No. 6825-20-3). In the first step, compound S1-1 is combined with hydrazine to form compound S1-2. In the second step, compound S1-3 is combined with n-butyl lithium (nBuLi) in hexanes at −78° C. prior to the addition of trimethylsilylchloride (TMSCl). The reaction is allowed to warm to room temperature and stir for 3 hours to form compound S1-4. Compounds S1-2 and S1-4 are combined in the presence of potassium phosphate ($K_3PO_4$), copper iodie (Cue, and toluene at 80° C. for 6 hours to create Compound No. 13. It is understood that steps 1, 2, and 3 can be performed and optimized by a person having ordinary skill in the art without undue experimentation.

Synthesis of Compound No. 9

Figure 3:
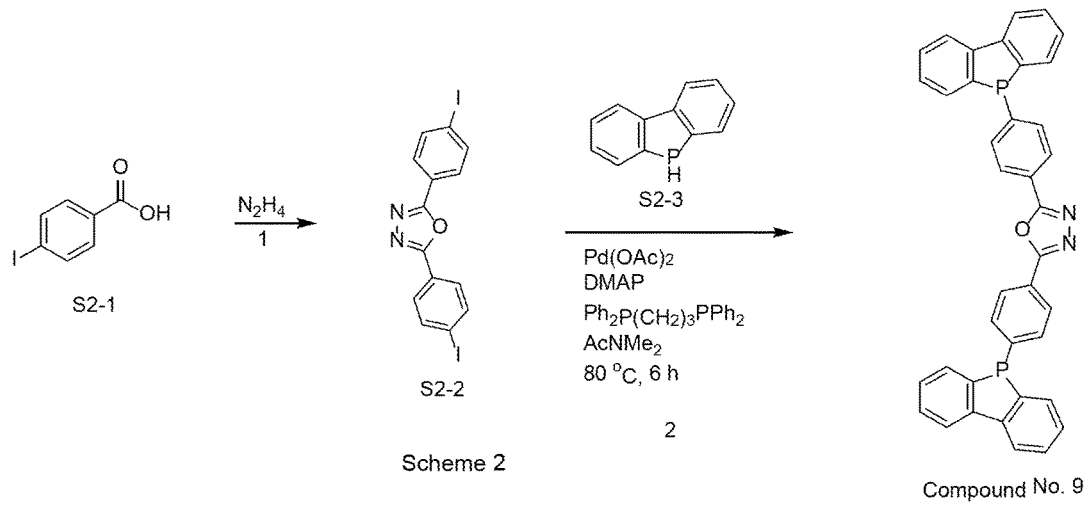
FIG. 3 is a synthetic scheme (Scheme 2) illustrating synthesis of an example embodiment of the present invention.

Compound No. 9 can be synthesized by a person of ordinary skill following Scheme 2 illustrated in FIG. 3. Compound S2-1 is available for purchase from Acros Organics (CAS No. 619-58-9). Compound S2-3 is available for purchase from Strem Chemicals, Inc. (CAS No. 244-87-1). In the first step, compound S2-1 is combined with hydrazine to form compound S2-2. In a second step, compound S2-2 is combined with compound S2-3 in the presence of $Pd(OAc)_2$, DMAP, $Ph_2P(CH_2)_3PPH_2$, and $AcNMe_2$ at 80° C. for 6 hours to form Compound No. 9. It is understood that steps 1 and 2 can be performed and optimized by a person having ordinary skill in the art without undue experimentation.

Synthesis of Compound No. 20

Figure 4:
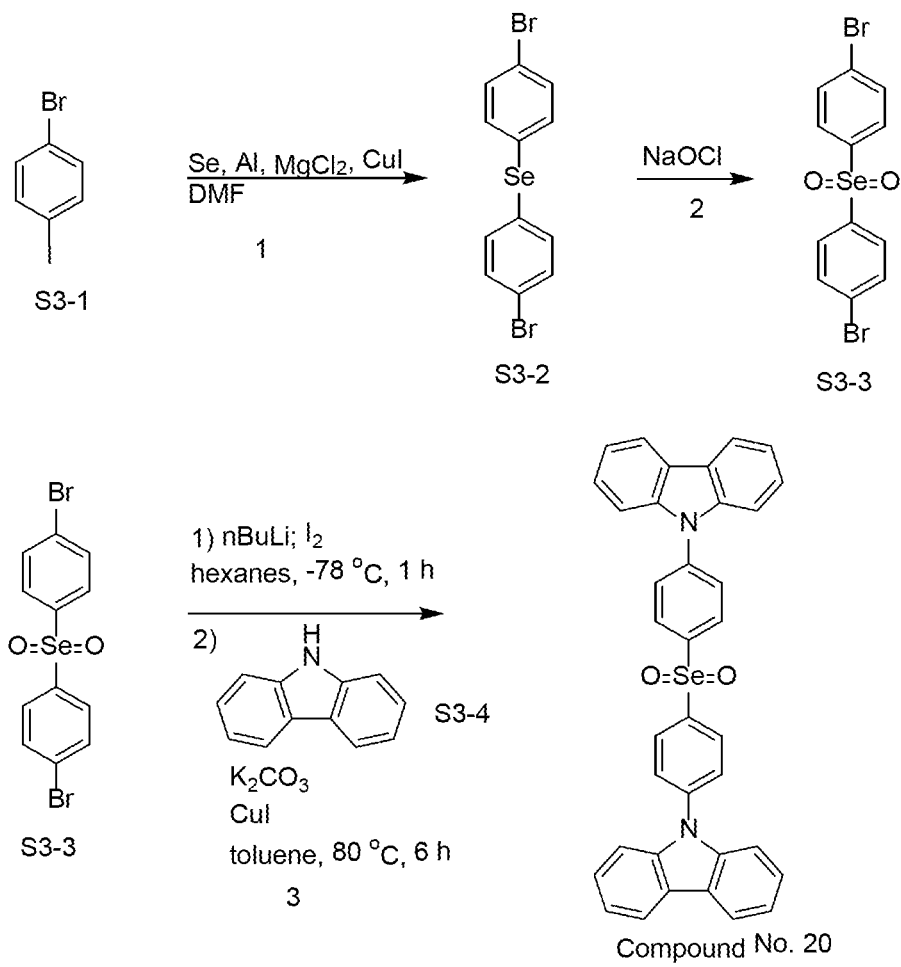
FIG. 4 is a synthetic scheme (Scheme 3) illustrating synthesis of an example embodiment of the present invention.

Compound No. 20 can be synthesized by a person of ordinary skill following Scheme 3 illustrated in FIG. 4. Compounds S3-1 and S3-4 can be purchased from Acros Organics (S3-1: CAS No. 589-87-7; S3-4: CAS No. 86-74-8). In the first step, compound S3-1 is combined with selenium in the presence of aluminum, magnesium chloride, copper iodide and DMF to produce compound S3-2. In the second step, compound S3-2 can be oxidized in the presence of sodium hypochlorite (NaOCl) to create compound S3-3. In the fourth step, compound S3-3 is combined with n-butyl lithium (nBuLi) in hexanes at −78° C. prior to the addition of iodine. The reaction is allowed to warm to room temperature and stir for 1 hour. The intermediate can be taken, without purification, and combined with compound S3-4 in the presence of potassium carbonate ($K_2CO_3$), copper iodide (CuI), and toluene at 80° C. for 6 hours to create Compound No. 20. It is understood that steps 1, 2, and 3 can be performed and optimized by a person having ordinary skill in the art without undue experimentation.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by any one of the following structural formulas:

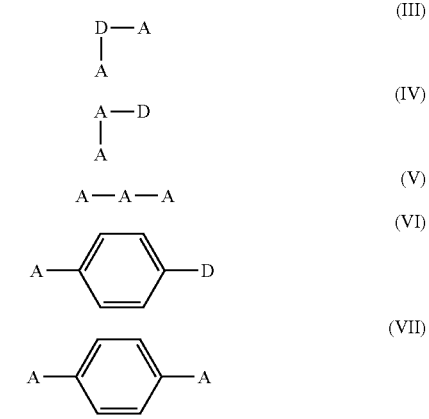

-continued

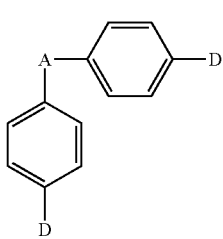
(VIII)

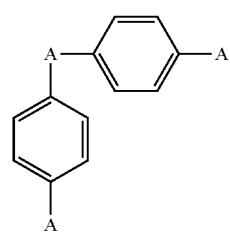
(IX)

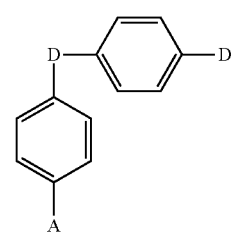
(X)

wherein each moiety D and each moiety A, independently, are selected from the group consisting of:

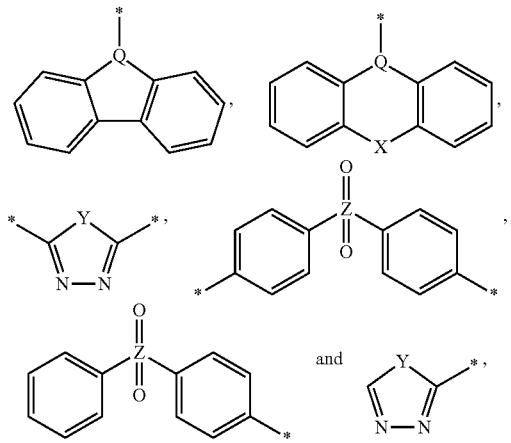

with the understanding that when more than one A or more than one D are present, all As and, independently, all Ds are the same,
wherein:
the (*) represents the point of attachment of the moieties A and D in the structural formulas (I) through (X);
Q is N, P, or As,
X is O, S, Se, —C(CH$_3$)$_2$, or —Si(CH$_3$)$_2$,
Y is O, S, or Se,
Z is S or Se,
wherein the moiety A and the moiety D, for each occurrence independently, are optionally substituted with one or more substituents selected from C$_1$-C$_6$alkyl,— OCH$_3$, —SCH$_3$, —C(CH$_3$)$_3$, —Si(CH$_3$)$_3$, —Ge(CH$_3$)$_3$, or —Sn(CH$_3$)$_3$; and wherein the molecule comprises at least one atom selected from Si, Se, Ge, Sn, P, or As.

2. The compound of claim 1, wherein the compound is represented by any one of the following structural formulas:

(III)

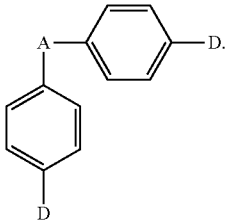
(VIII)

3. The compound of claim 1, wherein each moiety D and each moiety A, independently, are selected from the group consisting of:

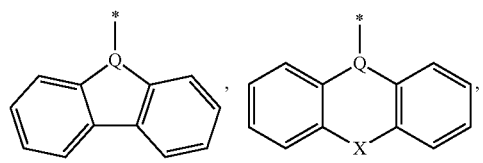

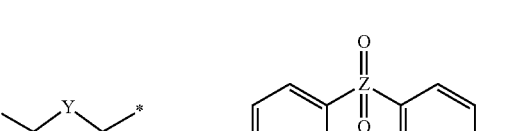

wherein the moiety A and the moiety D, for each occurrence independently, are optionally substituted with one or more substituents selected from C$_1$-C$_6$alkyl, —OCH$_3$, —SCH$_3$, —C(CH$_3$)$_3$, —Si(CH$_3$)$_3$, —Ge(CH$_3$)$_3$, or —Sn(CH$_3$)$_3$.

4. The compound of claim 3, wherein at least one of the moieties A or D is

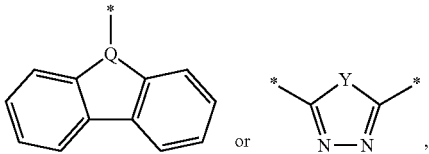

wherein the moiety A and the moiety D, for each occurrence independently, are optionally substituted with one or more substituents selected from C$_1$-C$_6$alkyl, —OCH$_3$, —SCH$_3$, —C(CH$_3$)$_3$, —Si(CH$_3$)$_3$, —Ge(CH$_3$)$_3$, or —Sn(CH$_3$)$_3$.

5. The compound of claim 4, wherein at least one of the moieties A or D is

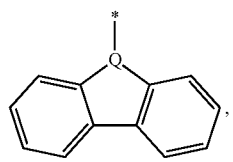

wherein the moiety A and the moiety D, for each occurrence independently, are optionally substituted with one or more substituents selected from $C_1$-$C_6$alkyl, —$OCH_3$, —$SCH_3$, —$C(CH_3)_3$, —$Si(CH_3)_3$, —$Ge(CH_3)_3$, or —$Sn(CH_3)_3$.

6. The compound of claim 4, wherein at least one of the moieties A or D is

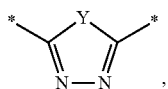

wherein the moiety A and the moiety D, for each occurrence independently, are optionally substituted with one or more substituents selected from $C_1$-$C_6$alkyl, —$OCH_3$, —$SCH_3$, —$C(CH_3)_3$, —$Si(CH_3)_3$, —$Ge(CH_3)_3$, or —$Sn(CH_3)_3$.

7. The compound of claim 3, wherein at least one of the moieties A or D is

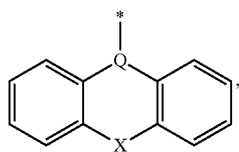

wherein the moiety A and the moiety D, for each occurrence independently, are optionally substituted with one or more substituents selected from $C_1$-$C_6$alkyl, —$OCH_3$, —$SCH_3$, —$C(CH_3)_3$, —$Si(CH_3)_3$, —$Ge(CH_3)_3$, or —$Sn(CH_3)_3$.

8. The compound of claim 7, wherein at least one of the moieties A or D is

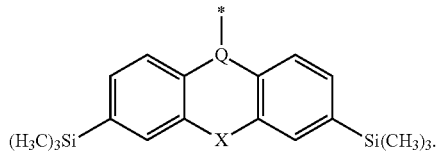

9. The compound of claim 3, wherein at least one of the moieties A or D is

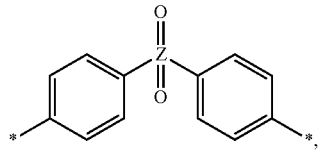

wherein the moiety A and the moiety D, for each occurrence independently, are optionally substituted with one or more substituents selected from $C_1$-$C_6$alkyl, —$OCH_3$, —$SCH_3$, —$C(CH_3)_3$, —$Si(CH_3)_3$, —$Ge(CH_3)_3$, or —$Sn(CH_3)_3$.

10. The compound of claim 1, wherein Z is Se.

11. The compound of claim 1, wherein Q is N or P.

12. The compound of claim 11, wherein Q is N.

13. The compound of claim 1, wherein X is O, —$C(CH_3)_2$, or —$Si(CH_3)_2$.

14. The compound of claim 13, wherein X is O or —$C(CH_3)_2$.

15. The compound of claim 14, wherein X is O.

16. The compound of claim 1, wherein Y is O or Se.

17. The compound of claim 16, wherein Y is Se.

18. The compound of claim 1, wherein the compound comprises at least one atom selected from Si, Se, or P.

19. The compound of claim 1, wherein the compound comprises at least one atom selected from Si or Se.

20. The compound of claim 1, wherein the compound comprises Si.

21. The compound of claim 1, wherein the moiety A and the moiety D, for each occurrence independently, are optionally substituted with $C_1$-$C_6$ alkyl, —$OCH_3$, —$C(CH_3)_3$, or —$Si(CH_3)_3$.

22. The compound of claim 21, wherein the moiety A and the moiety D, for each occurrence independently, are optionally substituted with $C_1$-$C_6$ alkyl or —$Si(CH_3)_3$.

23. The compound of claim 22, wherein the moiety A and the moiety D, for each occurrence independently, are optionally substituted with —$Si(CH_3)_3$.

24. A molecule represented by a structural formula selected from the group consisting of:

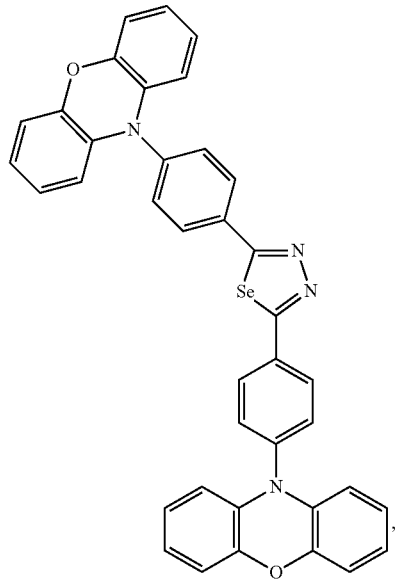

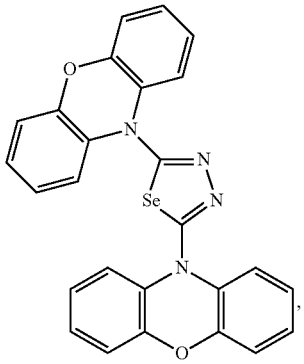
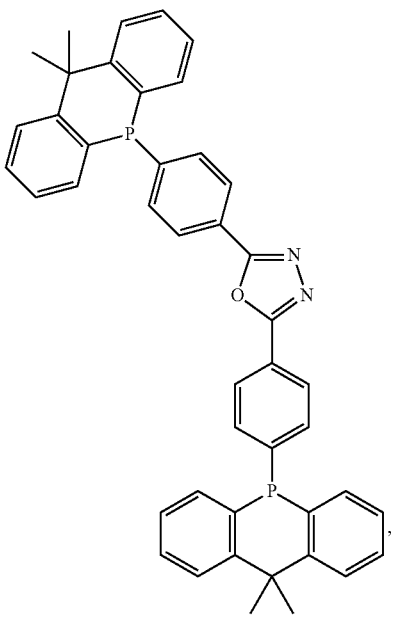
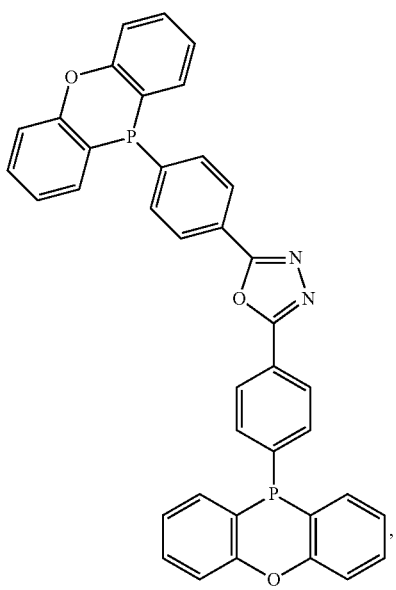
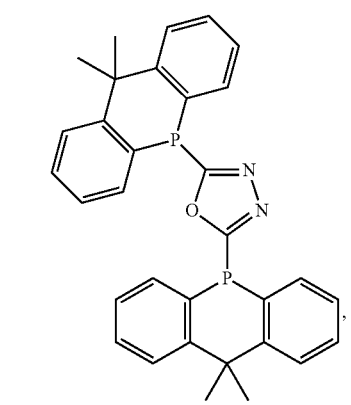
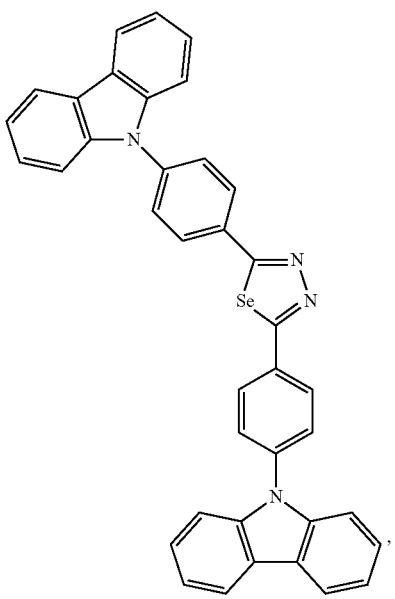

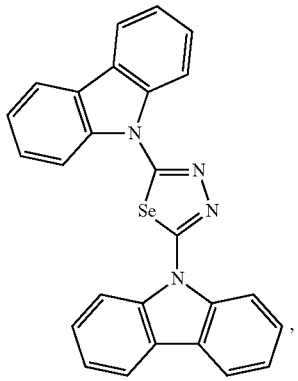
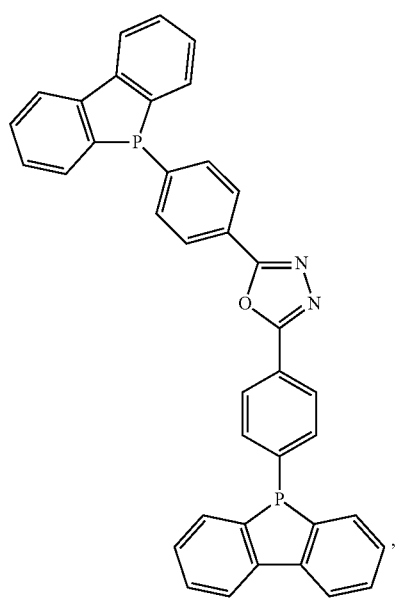
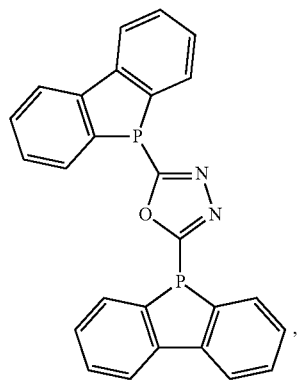
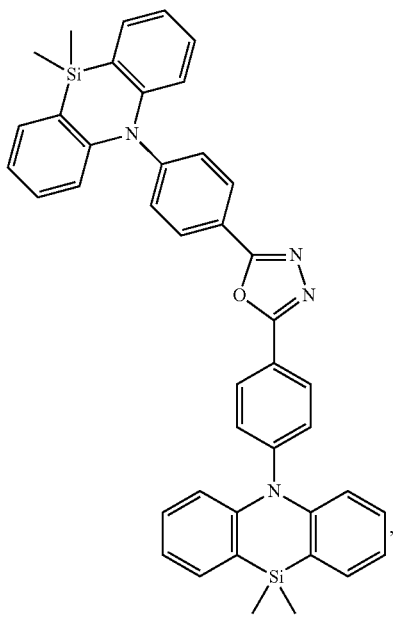
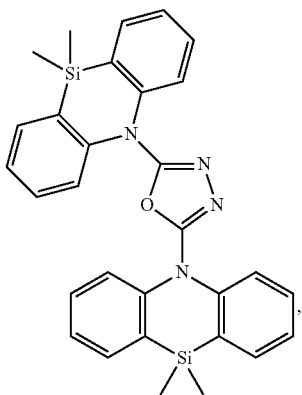
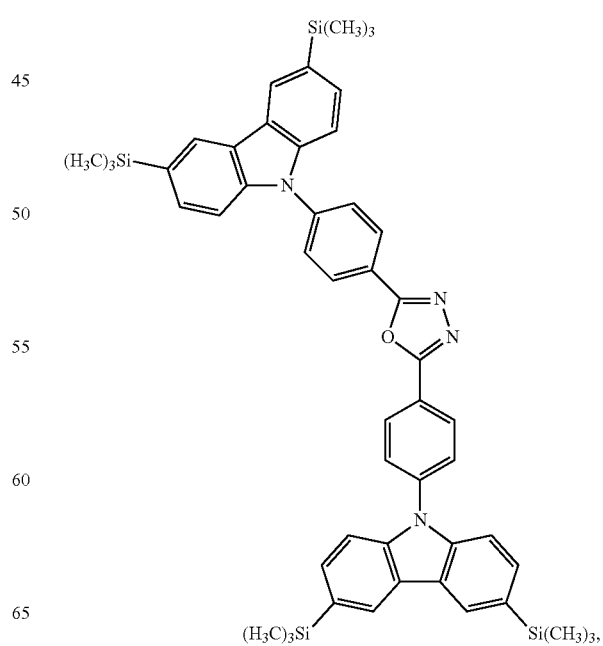

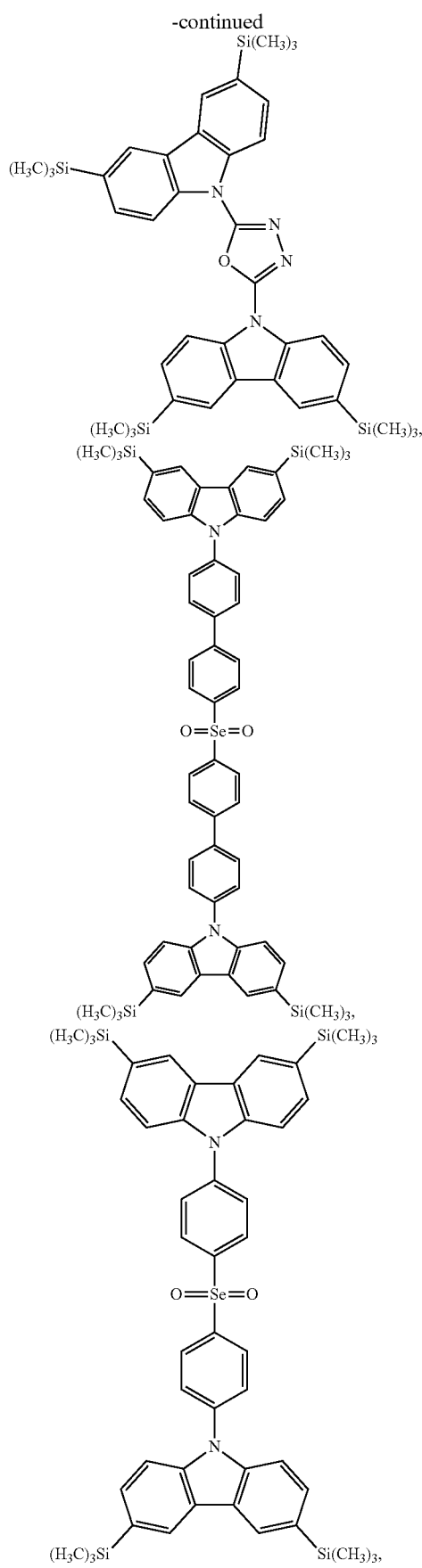
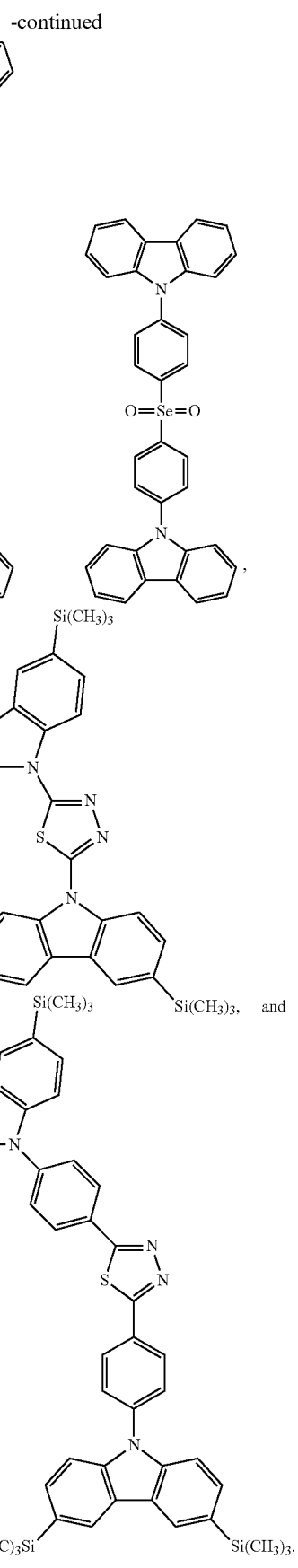

25. An organic light-emitting device comprising:
a first electrode;
a second electrode; and
an organic layer between the first electrode and the second electrode, and wherein the organic layer comprises at least one molecule of claim 1.

* * * * *